United States Patent [19]

Dyroff et al.

[11] 4,105,756

[45] Aug. 8, 1978

[54] INHIBITION OF DENTAL CALCULUS

[75] Inventors: David R. Dyroff, Creve Coeur, Mo.; Walton F. Suchanek, Jr., Belleville, Ill.

[73] Assignee: Monsanto Company, St. Louis, Mo.

[21] Appl. No.: 744,484

[22] Filed: Nov. 24, 1976

[51] Int. Cl.² .................... A61K 7/16; A61K 7/24; A61K 9/68; A61K 31/19
[52] U.S. Cl. ........................... 424/48; 424/49; 424/55; 424/317
[58] Field of Search ................... 424/48–58, 424/317

[56] References Cited

U.S. PATENT DOCUMENTS

| | | | |
|---|---|---|---|
| 3,542,917 | 11/1970 | Schwartz | 424/49 |
| 3,671,626 | 6/1972 | Felger | 424/49 |
| 3,865,755 | 2/1975 | Lannort | 260/535 P |
| 3,920,837 | 11/1975 | Schmidt-Dunker et al. | 424/49 X |

*Primary Examiner*—Shep K. Rose
*Attorney, Agent, or Firm*—S. M. Tarter; E. P. Grattan; F. D. Shearin

[57] ABSTRACT

Oral compositions such as mouth washes, toothpastes, foods, chewing gums and the like containing certain carboxyalkoxy-propanedioic acid compounds inhibit formation of dental calculus.

20 Claims, No Drawings

INHIBITION OF DENTAL CALCULUS

BACKGROUND OF THE INVENTION

The field of this invention is "oral compositions" which term herein means products intended for introduction into the oral cavity in such a manner as to contact exposed dental surfaces therein. Examples of such products are human and lower animal foods, chewing gums and oral hygiene products including mouth washes, prophylaxis pastes, topical solutions and dentifrices such as toothpastes, tooth powders, dental creams and the like.

Dental calculus, or tartar as it is sometimes called, is a deposit which forms on the surfaces of teeth predominantly at or near the gingival margin. Supragingival calculus appears most heavily in areas near the orifices of the salivary ducts. Mature calculus contains an inorganic portion which is largely calcium phosphate arranged in a hydroxyapatite crystal lattice structure similar to that occurring in bone, enamel or dentine. An organic portion is typically also present consisting of desquamated epithelial cells, salivary sediment, food debris, various types of microorganisms, etc.

As calculus develops, it becomes visibly white or yellowish unless stained or discolored by some extraneous substance. In addition to being undesirable from an esthetic standpoint, mature calculus deposits are sources of irritation of the gingiva and thereby a contributing factor to gingivitis and other diseases of the supporting structures of the teeth, the irritation decreasing the resistance of tissues to endogenous and exogenous organisms.

Periodic mechanical removal of this material by a dentist or dental technician is routine dental office procedure. There have also been proposed a number of chemical agents for calculus removal. For example, alkali metal and ammonium diglycolates and diglycolates of organic bases such as urea, guanidine or ethanolamine are suggested for that use in U.K. Pat. No. 995,330 issued June 16, 1965 to R. A. Oetker. Similarly, in U.S. Pat. No. 3,429,963 issued Feb. 25, 1969 to L. Shedlovsky, it is taught that dental calculus can be removed by use of dental preparations containing a hydrolyzed copolymer of ethylene and maleic anhydride having an average molecular weight of at least about 1500.

In some instances, chemical agents have been said to be capable of retarding calculus formation. For example, in the aforementioned U.S. Pat. No. 3,429,963 it is disclosed that a reduction in calculus formation was observed in rats when the drinking water given to the rats contained 1% of a hydrolyzed copolymer of ethylene and maleic anhydride. Another polymer, i.e., a polyester of a polycarboxylic acid having three or more carboxyl groups and a polyalkylene ether having at least two hydroxyl groups, is described as a calculus retarding agent in U.S. Pat. No. 3,542,917 issued Nov. 24, 1970 to A. M. Schwartz et al. In U.S. Pat. No. 3,920,837 issued Nov. 18, 1975 to M. Schmidt-Dunker et al, it is said that tartar formation can be substantially reduced by cyclohexanehexacarboxylic acid or its water-soluble salts. Various phosphorous compounds such as, e.g., ethane-1-hydroxy-1,1-diphosphonic acid (hereinafter EHDP), have also been proposed for such use in U.S. Pat. No. 3,488,419 issued Jan. 6, 1970 to H. W. McCune et al.

Some of the chemical agents heretofore proposed for calculus removal or retardation certain functional groups of uncertain effect on animals in terms of toxicity, side effects, etc. Certain other kinds of compounds containing only carbon, hydrogen, oxygen and possibly sodium, potassium or other pharmaceutically acceptable cations are believed essentially free from such uncertainty and therefore preferable for use in oral compositions. Also desirable for present purposes are compounds of relatively simple structure and low molecular weight, as well as compounds which can be prepared without resort to a polymerization process. Accordingly, oral compositions containing compounds which meet those criteria and which substantially inhibit dental calculus formation are highly desirable, and it is an object of this invention to provide such compositions. Other objects will be apparent from the following disclosure in which all percentages are by weight except where otherwise noted.

SUMMARY OF THE INVENTION

This invention is an oral composition effective in inhibiting formation of dental calculus, said composition comprising (1) a carboxyalkoxy-propanedioic acid compound selected from the group consisting of acids having the structural formula:

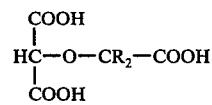

wherein R is hydrogen or lower alkyl, and pharmaceutically acceptable salts of said acids and (2) a carrier suitable for use in the oral cavity, said compound being present in said composition in amount and concentration sufficient to substantially inhibit formation of dental calculus.

DESCRIPTION OF PREFERRED EMBODIMENTS

In the foregoing structural formula each R can be the same as or different from the other R in that formula. Also as used herein, "lower alkyl" means $C_1$–$C_4$ alkyl groups which can be branched (e.g. isopropyl, isobutyl or tert-butyl) or cyclic (cyclopropyl or cyclobutyl) but which are preferably straight-chain (methyl, ethyl, n-propyl or n-butyl).

In some preferred embodiments of the invention R is hydrogen or normal alkyl, and in some of those embodiments it is very desirable that the number of carbon atoms in the —$CR_2$— radical is not greater than 5. In some embodiments it is preferred that one R in the —$CR_2$— radical is hydrogen and the other R in that radical is hydrogen, methyl or ethyl. Each of these embodiments is preferable on the basis of relatively low molecular weight. On the other hand, some compounds similar to those expressly included in that formula but wherein at least one of the R's in that formula contains more than four carbon atoms may similarly inhibit calculus formation when used in suitable oral compositions and in such cases should be regarded as equivalents of the aforementioned carboxyalkoxy-propanedioic acid compounds for purposes of this invention.

The carboxyalkoxy-propanedioic acid compounds represented by the foregoing formula when one R is hydrogen and the other R is hydrogen, methyl or ethyl are herein designated carboxymethoxy-propanedioic acid, 1-carboxyethoxy-propanedioic acid and 1-carboxypropoxy-propanedioic acid, respectively. Those three specific acids are hereinafter for convenience called CMPDA, CEPDA and CPPDA, respectively. The trisodium salts of those three acids and variations thereof when each R in the foregoing formula is methyl or ethyl can be prepared by procedure set forth in U.S. Pat. No. 3,865,755 issued Feb. 11, 1975 to Kent P. Lannert, the disclosure of which is incorporated herein by reference. The trisodium salts of other acids represented by that formula when at least one R is $C_3$–$C_4$ alkyl can be prepared by procedure analogous to that in U.S. Pat. No. 3,865,755 but in which an appropriate conjugate base of a lower alkyl ester of a more highly alkyl-substituted α-hydroxy acid (e.g. α-hydroxy-n-butyric, -isovaleric, -α-methyl-n-valeric or the like) is substituted for one of the α-hydroxy ester salt reactants suggested in that patent.

Any of the aforementioned carboxyalkoxy-propanedioic acid salts can be converted to the corresponding acid (e.g. CMPDA, CEPDA or CPPDA) by treatment with a strong acid, e.g. HCl, $H_2SO_4$ or a strongly acidic ion exchange resin. Other metal salts of the resulting acids can be prepared by neutralization with the appropriate metal hydroxide, e.g. an alkali metal hydroxide such as potassium hydroxide. The corresponding ammonium, mono- or di($C_1$–$C_3$ alkyl)ammonium or mono- or di($C_1$–$C_3$ alkanol)ammonium salts can be prepared by treating such acids with ammonia, an appropriate alkylamine or alkanolamine or hydroxide thereof in accordance with procedures well known in the art.

In the oral compositions of this invention, the proportions in which the aforementioned carboxyalkoxy-propanedioic acid compounds are present as acids and/or partially-substituted or fully-substituted salts thereof are dependent on the pH of the composition. That pH is normally between about 4 and about 11, although in some instances it may be higher or lower than that range. Below about pH 4 there is a greater danger of damage to dental enamel despite the relative safety of the aforementioned acid or its salts. Above about pH 11, greater difficulty is encountered in formulating products having satisfactory flavor and mildness. A preferred pH range is from about 6 to about 10. In many embodiments, the pharmaceutically acceptable salts employed are preferably water-soluble salts such as, e.g., sodium, potassium or ammonium salts, to facilitate their dissolution in saliva.

Some embodiments of this invention are oral hygiene products such as dentifrices, mouth washes, prophylaxis pastes and topical solutions. A dentifrice, especially toothpaste, containing a calculus-inhibiting amount of an acid represented by the foregoing structural formula and/or a pharmaceutically acceptable salt thereof is a preferred embodiment of this invention. A mouth wash containing such an acid and/or salt is another preferred embodiment. Except for inclusion of a carboxyalkoxy-propanedioic acid compound as described hereinbefore, many formulations of such products are well known in the art. For example, typical formulations of toothpastes and mouth washes compatible with calculus-inhibiting compounds of the kind employed in accordance with this invention are described in U.S. Pat. No. 3,639,569 issued Feb. 1, 1972 to R. F. Medcalf, Jr., U.S. Pat. No. 3,544,678 issued Dec. 1, 1970 to W. J. Griebstein, U.S. Pat. No. 3,678,154 issued July 18, 1972 to J. S. Widder et al and U.S. Pat. No. 3,959,458 issued May 25, 1976 to F. O. Agricola et al, the disclosures of which are incorporated herein by reference.

Under conditions of normal use, the oral compositions of this invention are pharmaceutically acceptable, i.e., capable of introduction into the oral cavity without significant adverse effect on tooth structure or other injury to health. Subject to the limits of such pharmaceutical acceptability, the calculus-inibiting amounts and concentrations of the aforementioned carboxyalkoxy-propanedioic acid compounds can be varied widely in the oral compositions of this invention and are readily definable for each kind of oral composition by formulators skilled in the art. Generally, concentrations between about 0.01% and about 10% are preferred. Oral compositions which in ordinary usage may be accidentally or intentionally ingested can contain relatively low but still highly effective concentrations. Of course, any such ingested composition should be physiologically (i.e., digestively) acceptable. Thus, a mouth wash in accordance with this invention preferably contains between about 0.1% and about 3% of the aforementioned calculus-inhibiting compound. Dentifrice compositions, topical solutions and prophylaxis pastes, the last normally administered professionally, may desirably contain up to about 10% or even more thereof but usually contain between about 0.1% and about 5% and even more typically between about 1% and about 2% thereof.

While it is not intended that this invention be limited to any particular theory of operation, it has been observed that the aforementioned carboxyalkoxy-propanedioic acid compounds appear to inhibit calculus formation by interfering with the conversion of dissolved calcium phosphate in saliva to crystalline deposits in the nature of calcium hydroxyapatite. Hence the compositions of this invention preferably do not contain soluble polyvalent cations in an amount likely to deplete the crystal growth inhibiting capacity of those compounds to the extent that their calculus formation inhibiting activity would be essentially neutralized.

The following specific examples are illustrative only and do not imply any limitations on the scope of the invention.

EXAMPLES I–V

A. Evaluations of Calculus Inhibition

Evaluations of the effectiveness of compounds employed in accordance with this invention to inhibit calculus formation were carried out fundamentally as described in "A Method and Apparatus for Studying In Vitro Calculus" by S. Yankelowitz et al of the Colgate-Palmolive Co., Journal of Dental Research 44 (No. 4), 648–53 (1965). In accordance with that method, now well known in the art, simulated oral calculus deposits are caused to be formed on glass slides by mechanically rotating the slides edgewise and vertically at 0.5 rpm in such a way that each slide passes alternately through a small sample of whole human saliva containing 0.1% of added monocalcium phosphate and then through a forced draft of air which at least partially dries each slide before it passes again through that saliva sample. As stated in the journal article just mentioned, the resulting calculus deposits have been found similar to oral calculus deposits in both composition and X-ray diffraction pattern.

In each of the present evaluations, 150 mls of stimulated saliva were collected over a three-day period (50 ml/day) from a donor whose saliva had been previously found to have a substantial tendency toward calculus formation. The collected saliva was also of a type in which, under the conditions of this test, calculus formation is inhibited by EHDP substantially more than by water substituted for the EHDP in a comparative test run. Each 50 ml portion of the saliva was kept frozen until ready for use. At that time the combined 150 ml sample was neutralized to pH 7±0.05 after addition of the 0.1% of mono-calcium phosphate, thoroughly stirred and then divided into 25 ml aliquots. To one aliquot was added 1 ml of a 0.1 M solution of the trisodium salt of CMPDA, CEPDA or CPPDA, and to a second aliquot was added 1 ml of a 0.1 M solution of the prior art anti-calculus compound EHDP, each of those solutions having been previously neutralized with NaOH or $H_2SO_4$. To a third aliquot was added 1 ml of distilled water.

For comparative test purposes, the three aliquots were then placed in identical side-by-side trough-like containers in an oven equipped with apparatus adapted to rotate a separate set of three 22 × 40 mm glass slides (spaced about 120° apart in relation to the rotaing shaft on which they were mounted) through each of the saliva containers and to maintain a steady horizontal flow of air against the slides and perpendicular to the axis of their rotation. All slides used were essentially identical and mounted on the shaft such that the same portion (24 mm) of the length of each slide passed through the appropriate saliva sample.

In the oven just described, the calculus formation test was continued for 20 consecutive hours with the interior of the oven maintained at 37° ± 1° C and a relative humidity between 76 and 78%. The saliva samples were then removed from the oven, after which rotation of the slides in the flow of air was continued for an additional hour before removal of the slides from the oven. The weight of each slide and any deposit remaining thereon was then compared with the weight of the slide prior to its use in this test, and visual appraisals of the deposits were made using photographs taken of each slide under identical conditions to further eliminate variables from those appraisals. Results were recorded separately for each of the three slides in each set and then averaged. Thereafter, the entire procedure was repeated (twice in the case of the CMPDA salt) using saliva from a different donor in each case, and the results of the several runs were averaged to provide the results reported hereinafter.

1. CMPDA

In the tests of the trisodium salt of CMPDA it was found that the weights of simulated calculus on the slides that had been exposed to the salivas containing that salt averaged 1.00 mg, those of the slides used in the comparative runs with EHDP averaged 0.62 mg, and those on the slides used in the comparative runs with water averaged 1.48 mg. Thus in the runs using that salt of CMPDA, formation of the simulated calculus averaged 32% less than in the comparative runs using water, while in the comparative runs using EHDP it averaged 58% less than in the comparative runs using water. In the visual appraisal, the amounts of opaque material deposited on the slides that had been exposed to the salivas containing the sodium salt of CMPDA were judged to be, on average, below 33 on an essentially linear scale in which 100 represents the amount of opaque material on the slides used in the comparative runs with water and 0 represents the amount of such material on the slides used in the comparative runs with EHDP. Also in the visual appraisal, the amounts of opaque material deposited on the slides exposed to the salivas containing the CMPDA salt were judged to be, on average, less than half as great as those on the slides used in the comparative runs with water.

2. CPPDA

In the tests of the trisodium salt of CPPDA it was found that the weights of simulated calculus on the slides that had been exposed to the salivas containing that salt averaged 0.34 mg, those on the slides used in the comparative runs with EHDP averaged 0.27 mg, and those on the slides used in the comparative runs with water averaged 0.55 mg. Thus in the runs using the CPPDA salt, formation of the simulated calculus averaged 38% less than in the comparative runs using water, while in the comparative runs using EHDP it averaged 51% less than in the runs using water. In the visual appraisal, the amounts of opaque material deposited on the slides that had been exposed to the salivas containing the CPPDA salt were judged to be, on average, substantially below 25 on the scale of 0 to 100 described in the preceding paragraph herein and less than half as great as those on the slides used in the comparative runs with water.

3. CEPDA

In the tests of the trisodium salt of CEPDA it was found that the weights of the deposits on the slides that had been exposed to the salivas containing that salt averaged 0.83 mg, those on the slides used in the comparative runs with EHDP averaged 0.17 mg, and those on the slides used in the comparative runs with water averaged 0.60 mg. Thus in the runs using the CEPDA salt, the weights of the deposits averaged 38% more than in the comparative runs using water, while in the comparative runs using EHDP they averaged 72% less than in the runs using water. In the visual appraisal, the amounts of opaque material deposited on the slides that had been exposed to the salivas containing the CEPDA salt were judged to be, on average, no higher than 25 on the scale of 0 to 100 described hereinbefore and less than half as great as those on the slides used in the comparative runs with water.

B. Preparation of Oral Compositions

The compounds tested in Part A of these examples, the corresponding acids and other pharmaceutically acceptable salts of those acids are useful for inhibition of dental calculus formation when incorporated in compatible carriers or vehicles of any of the usual types. The following are examples of mouth wash compositions comprising at least one of such compounds.

|  | Examples | | | |
|---|---|---|---|---|
|  | I | II | III | IV |
| Component | Parts by weight | | | |
| Glycerine | 10.0 | 10.0 | 10.0 | 10.0 |
| Ethyl alcohol | 16.5 | 16.5 | 16.5 | 16.5 |
| Water | 67.172 | 67.172 | 67.172 | 70.192 |
| Tween 80[1] | .12 | .12 | .12 | .12 |
| Saccharin | .045 | .045 | .045 | .02 |
| Sodium cyclamate | 0.75 | 0.75 | 0.75 | .04 |
| Flavor | .088 | .088 | .088 | .088 |
| Salt of CMPDA, CEPDA or CPPDA | [2]3.0 | [3]4.0 | [4]2.0 | [5]1.8 |

| Component | Examples | | | |
|---|---|---|---|---|
| | I | II | III | IV |
| | Parts by weight | | | |
| pH[6] | 7.0 | 7.0 | 8.5 | 10.0 |

[1] Polyoxyethylene (20 moles of ethylene oxide) sorbitan mono-oleate - a nonionic emulsifier supplied by Atlas Powder Co.
[2] Triammonium salt.
[3] Tri(triethanolammonium) salt.
[4] Trisodium salt.
[5] Tripotassium salt.
[6] Adjusted to value indicated with NaOH or $H_2SO_4$.

The following is an example of a toothpaste composition comprising at least one of such compounds.

| Component | Example V |
|---|---|
| | Parts by weight |
| Water | 31.58 |
| Sorbitol | 6.25 |
| Saccharin | 0.12 |
| Calcium pyrophosphate[1] | 39.00 |
| Glycerine | 18.00 |
| Sodium alkyl (coconut) sulfate | 0.40 |
| Sodium coconut monoglyceride sulfonate | 0.75 |
| Sodium carboxymethyl cellulose | 1.15 |
| Magnesium aluminum silicates | 0.40 |
| Flavoring | 0.85 |
| CMPDA, CEPDA or CPPDA | 1.00 |
| pH[2] | 5.90 |

[1] Prepared in accordance with U.S. Pat. 3,112,247 granted November 26, 1963.
[2] Adjusted to indicated pH with sodium hydroxide.

Other examples of toothpaste compositions comprising at least one of the aforementioned carboxyalkoxy-propanedioic acid compounds are essentially the same as the toothpaste composition above except for substitution of the corresponding potassium or ammonium salt of CMPDA, CEPDSA or CPPDA or a sodium, potassium or ammonium salt of (1-methyl,1-carboxyethoxy)-propanedioic acid or (1-methyl,1-carboxypropoxy)-propanedioic acid therein.

Additional examples of oral compositions comprising at least one of such compounds include other mouth washes and toothpastes, tooth powders, dental creams and prophylaxis pastes for use by a dentist or dental technician in polishing of teeth after removal of calculus deposits. Examples of such compositions, except for inclusion of a calculus-inhibiting compound of the kind used in accordance with the present invention, are described in the aforementioned U.S. Pat. Nos. 3,544,678, 3,639,569, 3,678,154 and 3,959,458. Typically, toothpastes are aqueous compositions containing a polishing agent, a surfactant, a binder, a humectant, a preservative, flavoring and sweetening agents and optionally therapeutic agents. Mouth washes typically contain water, ethanol, flavoring, sweetening and coloring agents and optionally a surfactant. Other examples of oral compositions comprising at least one of the compounds used in accordance with this invention include human foods such as soft drinks, candies, pastries, etc., foods for pets or livestock, chewing gums, etc. Chewing gums typically contain base materials, plasticizers or softeners, sugar or other suitable carbohydrates such as glucose, sorbitol, etc. Sugarless gums may contain other sweetening agents such as saccharin or sodium cyclamate. The ingredients of each of the foregoing oral compositions, other than the aforementioned carboxyalkoxy-propanedioic acid compounds, as well as various mixtures of such ingredients are illustrative of carriers suitable for use in the oral cavity in accordance with the present invention.

The embodiments of this invention in which an exclusive property or privilege is claimed are defined as follows:

1. An oral composition effective in inhibiting formation of dental calculus, said composition comprising (1) a carboxyalkoxy-propanedioic acid compound selected from the group consisting of acids having the structural formula:

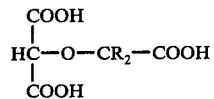

wherein each R is hydrogen or lower alkyl, and pharmaceutically acceptable salts of said acids and (2) a carrier suitable for use in the oral cavity, said compound being present in said composition in amount and concentration sufficient to substantially inhibit formation of dental calculus.

2. A composition according to claim 1 wherein said carrier comprises a dental polishing agent, flavoring agent, chewing gum base material, or human or animal food.

3. A composition according to claim 1 wherein each R is hydrogen or lower normal alkyl and the number of carbon atoms in the —$CR_2$— radical is not greater than 5.

4. A composition according to claim 3 wherein one R is hydrogen and the other R is hydrogen, methyl or ethyl.

5. An oral hygiene composition according to claim 4.

6. A chewing gum composition according to claim 4 wherein said carrier comprises a chewing gum base material.

7. A food composition according to claim 4 to be ingested by humans or lower animals.

8. A composition according to claim 4, said compound being selected from the group consisting of alkali metal and ammonium salts of said acids.

9. A composition according to claim 8 wherein each R is hydrogen.

10. An oral hygiene composition according to claim 9.

11. A mouth wash composition according to claim 9 having a pH between about 4 and about 11 wherein said carrier comprises a flavoring agent.

12. A toothpaste composition according to claim 9 having a pH between about 4 and about 11 wherein said carrier comprises a dental polishing agent or a flavoring agent.

13. A composition according to claim 8 wherein one R is methyl.

14. An oral hygiene composition according to claim 13.

15. A mouth wash composition according to claim 13 having a pH between about 4 and about 11 wherein said carrier comprises a flavoring agent.

16. A toothpaste composition according to claim 13 having a pH between about 4 and about 11 wherein said carrier comprises a dental polishing agent or a flavoring agent.

17. A composition according to claim 8 wherein one R is ethyl.

18. An oral hygiene composition according to claim 17.

19. A mouth wash composition according to claim 17 having a pH between about 4 and about 11 wherein said carrier comprises a flavoring agent.

20. A toothpaste composition according to claim 17 having a pH between about 4 and about 11 wherein said carrier comprises a dental polishing agent or a flavoring agent.

* * * * *

UNITED STATES PATENT AND TRADEMARK OFFICE
CERTIFICATE OF CORRECTION

PATENT NO. :   4,105,756
DATED      :   August 8, 1978
INVENTOR(S):   David R. Dyroff, Walton F. Suchanek, Jr. and Thomas G. Schiff It is certified that error appears in the above—identified patent and that said Letters Patent are hereby corrected as shown below:

On the cover page, first column, under [75] Inventors: the name of THOMAS G. SCHIFF of Clayton, Missouri has been omitted as an inventor.

Signed and Sealed this

Thirteenth Day of February 1979

[SEAL]

Attest:

RUTH C. MASON
Attesting Officer

DONALD W. BANNER
Commissioner of Patents and Trademarks